(12) United States Patent
Baughman et al.

(10) Patent No.: US 8,688,309 B2
(45) Date of Patent: Apr. 1, 2014

(54) ACTIVE AND STATEFUL HYPERSPECTRAL VEHICLE EVALUATION

(75) Inventors: Aaron K. Baughman, Silver Spring, MD (US); Barry M. Graham, Silver Spring, MD (US); Rick A. Hamilton, II, Charlottesville, VA (US); Brian M. O'Connell, Research Triangle Park, NC (US)

(73) Assignee: International Business Machines Corporation, Armonk, NY (US)

( * ) Notice: Subject to any disclaimer, the term of this patent is extended or adjusted under 35 U.S.C. 154(b) by 150 days.

(21) Appl. No.: 13/316,831

(22) Filed: Dec. 12, 2011

(65) Prior Publication Data
US 2013/0151063 A1 Jun. 13, 2013

(51) Int. Cl.
*G01M 17/00* (2006.01)

(52) U.S. Cl.
USPC .......................................... 701/29.1; 702/188

(58) Field of Classification Search
USPC ................ 701/29.1, 46, 45, 40; 702/185, 188
See application file for complete search history.

(56) References Cited

U.S. PATENT DOCUMENTS

| | | | |
|---|---|---|---|
| 5,625,751 A * | 4/1997 | Brandwajn et al. | 706/20 |
| 7,363,111 B2 | 4/2008 | Vian et al. | |
| 2003/0004629 A1 * | 1/2003 | Cooper et al. | 701/45 |
| 2004/0078171 A1 | 4/2004 | Wegerich et al. | |
| 2004/0243351 A1 * | 12/2004 | Calkins et al. | 702/185 |
| 2006/0253282 A1 | 11/2006 | Schmidt et al. | |
| 2006/0293817 A1 * | 12/2006 | Hagiwara et al. | 701/40 |
| 2008/0243439 A1 * | 10/2008 | Runkle et al. | 702/188 |
| 2011/0238606 A1 * | 9/2011 | Ide | 706/12 |
| 2012/0143431 A1 * | 6/2012 | Kim et al. | 701/29.1 |

\* cited by examiner

*Primary Examiner* — Helal A Algahaim
*Assistant Examiner* — Shardul Patel
(74) *Attorney, Agent, or Firm* — Douglas A. Lashmit; Hoffman Warnick LLC

(57) ABSTRACT

A system, method and program product for evaluating a vehicle. A system is disclosed that includes: a plurality of hyperspectral sensors located in the vehicle; a system for fusing hyperspectral sensor data with user data into a feature vector; a support vector machine having a set of models, wherein the support vector machine implements a selected model based on the feature vector and outputs an evaluation based on data in the feature vector and the selected model; and a system for training the set of models.

20 Claims, 2 Drawing Sheets

ACTIVE AND STATEFUL HYPERSPECTRAL VEHICLE EVALUATION

BACKGROUND

The present invention relates to evaluating vehicle operations, and more particularly relates to characterizing the operational state of a vehicle based on acoustic signatures and other user information.

Currently, the operational state of a vehicle may be determined using various systems and information. For example, on-board sensors and detection mechanisms can detect problems and errors, e.g., low oil, overheating, flat tire, etc. Often times however, the operator is unaware of a potential or "brewing" problem until after a serious condition presents itself. Moreover, certain types of issues may be more likely to occur based on environmental factors, such as the weather.

BRIEF SUMMARY

In a first aspect, the invention provides a system for evaluating a vehicle, comprising: a plurality of hyperspectral sensors located in the vehicle; a system for fusing hyperspectral sensor data with user data into a feature vector; a support vector machine having a set of models, wherein the support vector machine implements a selected model based on the feature vector and outputs an evaluation based on data in the feature vector and the selected model; and a system for training the set of models.

In a second aspect, the invention provides a program product stored on a computer readable storage medium for evaluating a vehicle, comprising: program code for obtaining hyperspectral sensor data from hyperspectral sensors located in the vehicle; program code for fusing the hyperspectral sensor data with user data into a feature vector; program code for implementing a support vector machine having a set of models, wherein the support vector machine implements a selected model based on the feature vector and outputs an evaluation based on data in the feature vector and the selected model; and program code for training the set of models.

In a third aspect, the invention provides a method of evaluating a vehicle, comprising: obtaining hyperspectral sensor data from hyperspectral sensors located in the vehicle; fusing the hyperspectral sensor data with user data into a feature vector; and providing a support vector machine having a set of models, wherein the support vector machine implements a selected model based on the feature vector and outputs an evaluation based on data in the feature vector and the selected model.

BRIEF DESCRIPTION OF THE SEVERAL VIEWS OF THE DRAWINGS

These and other features of this invention will be more readily understood from the following detailed description of the various aspects of the invention taken in conjunction with the accompanying drawings.

Figure 1:
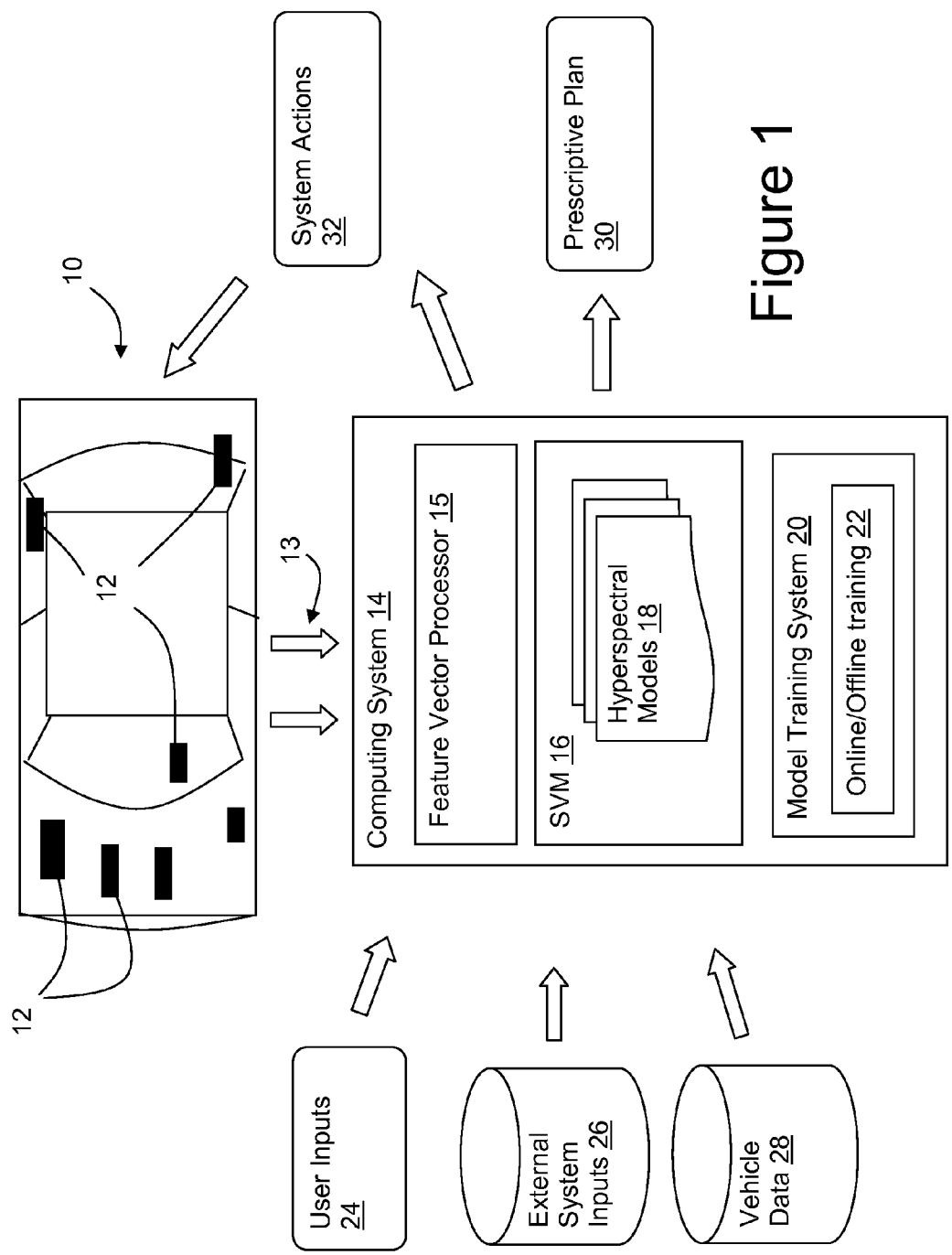
FIG. 1 depicts a system for evaluating a vehicle in accordance with an embodiment of the present invention.

The drawings are merely schematic representations, not intended to portray specific parameters of the invention. The drawings are intended to depict only typical embodiments of the invention, and therefore should not be considered as limiting the scope of the invention. In the drawings, like reference numbering represents like elements.

DETAILED DESCRIPTION

FIG. 1 depicts a vehicle 10 that includes a plurality of hyperspectral sensors (represented as black boxes) 12, that collect hyperspectral data. Hyperspectral data may include any type of detected frequency information but particularly includes at least acoustic data. Collected sensor data 13 is fed into a computing system 14 to, among other things, evaluate the vehicle, e.g., help detect and diagnose vehicle problems. Computing system 14 may be implemented on the vehicle 10 itself, externally (e.g., on a grid computing infrastructure), or a combination of the two. In addition to obtaining sensor data 13, computing system 14 may also utilize user inputs 24, external system inputs 26 and vehicle data 28.

User inputs 24 may for example comprise any information provided by an operator of the vehicle. Examples may include operator preferences or feedback regarding the vehicle, e.g., traction control preferences, performance preferences, steering preferences, etc. User inputs 24 may also include metadata information regarding the vehicle's operation, such as type of gas being utilized, number of passengers in the vehicle, weight of cargo, etc. External system inputs 26 may include additional information, such as relevant ecosystem information, including current weather conditions where the vehicle is being operated, smog levels, etc. Vehicle data 28 may include any information about the vehicle 10, such as maintenance history, type of equipment on the vehicle, oil type, recall information, tire pressures, etc. Differing features may be accounted for within a given vehicle, and sub-models or model facets built up accordingly. For instance, a given vehicle may be equipped with different tires or after-market parts such as exhausts, struts, shocks, or other units which may vary the signatures provided from a specific region of the vehicle. Such features may be a user-selected option, or may be automatically applied based on vehicle history and available canonical information.

Computing system 14 manages all of the different inputs with a feature vector processor 15 that fuses the different types of input into a feature vector having a predefined structure. For example, the feature vector may be encoded in an XML file or data structure having a protocol to store all possible data inputs. The feature vector may be made up of sub-vectors that include subsets of information, e.g., a first sub-vector may comprise acoustic data, a second sub-vector may comprise ecosystem data, etc.

Hyperspectral sensors 12, including acoustic sensors, are placed at strategic locations on the vehicle 10 to obtain hyperspectral stimuli. For example, an audio acquisition sensor may simply capture an audio stimulus created from an automotive component, being transmitted as sound waves in the current environment. The captured data is much like the otoacoustic audio response that occurs by an audio stimulus entering the ear in the form of sound waves, which then excites the inner ear hairs and triggers a tympanic membrane response. This causes a sound wave to travel back through the ear, with the ear producing sound. The same type of sound is produced by the body of the vehicle. Each type of sound yields an entry into a feature vector that is used to determine a state of the vehicle.

There are several types of hyperspectral stimuli that can be obtained, including data obtained: (1) in a passive mode (e.g., by listening) and (2) in an active mode (e.g., a frequency sound is emitted and the sensor 12 detects changes). According to the Lombard effect, all of the moving parts of a vehicle, including integrated circuits, have a frequency spectrum emission. In general, when something is starting to break down in the vehicle 10, multiple frequency spectrum emissions will change.

With respect to the practical workability of the described approach, it is recognized that most vehicle noises are found within a given spectrum. Upon signal analysis and processing (e.g., Fast Fourier Transforms or FFT's) to get to the frequency representation, noise can be reduced to, e.g., filter out human noise, external noises, etc. In addition, the closer the sensors 12 are to the sound source, the more gain the signal will have, and hence another type of filter can be applied to the amplitude.

Once a feature vector is created, a support vector machine (SVM) 16 is utilized to analyze the feature vector based on hyperspectral models 18. The support vector machine 16 projects feature vectors into a linear or non-linear state space using a kernel function or functions. The kernel function selects the type of hyperspectral model 18 to analyze with respect to the type of information input into the computing system 14. The support vector machine 16 is stateful such that previous states are known which thus yields temporal information. The support vector machine 16 acts as a multidimensional look-up table for pattern recognition of known hyperspectral models 18. Thus, as feature vectors are obtained, the support vector machine 16 matches the vehicle's conditions (e.g., acoustic data, ecosystem data, user feedback, etc.) with one or more hyperspectral models 18. Based on the hyperspectral model 18 that most closely maps to the collected feature vectors, an evaluation, e.g., diagnostic and other information associated with the model can be provided. As a result, the vitality monitoring is stateful over time and personalized to the vehicle 10 and operator.

In one embodiment, computing system 14 may output a prescriptive plan 30 for the user. The prescriptive plan 30 may include: proposed maintenance such as change the oil, rotate the tires, etc.; suggested driving techniques such as slow down while turning, stop riding the clutch, let the car warm up before driving, etc.; operator tests such as race the engine in neutral for several seconds; etc. In another embodiment, computing system 14 may output a set of system actions 32 that can be fed back directly to the vehicle 10. Examples may include adjusting air-to-fuel ratios, changing the shifting between gears, etc.

Computing system 14 also includes a model training system 20 that allows for both offline and online training 22. Hyperspectral models 18 of vehicles 10 in varying conditions and from differing acquisition locations may be trained by, e.g., independent organizations, service providers, manufacturers, dealerships, consumers, etc. Each model 18 may be built and then tagged with the conditions of which it was trained such as weather, car problems, etc. The models 18 can be trained online (real-time) or offline (asynchronously). Online training updates models 18 within a training environment. Once complete the training models 18 are hosted on a production environment. The models 18 could be, but are not limited to, Hidden Markov Models, Neural Networks, SVM's, Clustering Algorithms, Hopfield Networks, Belief Networks, and Baysian algorithms.

It should be noted that many alternate embodiments may be possible without departing from the scope of the proposed invention. For example, a social aspect may be added to aid in diagnostics. If the computing system 14 proposes a response that is incorrect, the user may note the information, along with what lead to the initial diagnosis which may be sent to a central system. If enough feedback is provided, the central system can update its models 18 to reduce false diagnostics.

Figure 2:
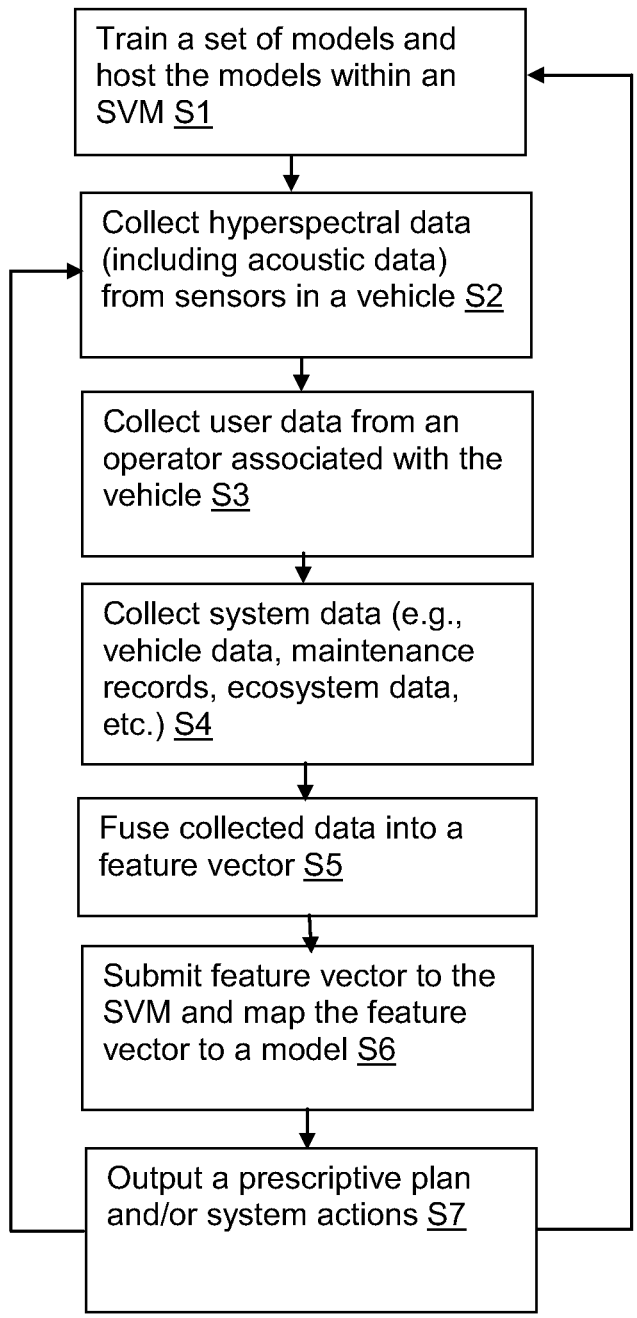
FIG. 2 depicts a flow diagram of a method of evaluating a vehicle in accordance with an embodiment of the present invention.

FIG. 2 depicts a flow chart showing an illustrative methodology. At S1, hyperspectral models are trained and the hosted within a support vector machine (SVM). At S2, hyperspectral data (including acoustic data) is collected from sensors in a vehicle. At S3, user data is also collected from an operator associated with the vehicle. User data may include, e.g., driving preferences, feedback, driving style, etc. At S4, system data is also collected, e.g., vehicle data, maintenance records, ecosystem data, etc. At S5, all of the data is fused into a feature vector and at S6 the feature vector is fed into the SVM. The feature vector is mapped to one of the trained models. Based on the selected model, and collected data an evaluation, e.g., a prescriptive plan and/or system actions, are outputted at S7.

The proposed embodiments accordingly combine ecological and vehicle self awareness using computer processing, which may be on-board or achieved via an external computational grid. A computational infrastructure may provide real-time algorithm processing for a vehicle evaluation. The evaluation is available to both the vehicle and operator. Over time, the models adapt to the vehicle, weather, and other conditions. As a result, vitality monitoring is stateful over time and personalized to the vehicle and operator. A core source of the vehicle features is acquired by any type of hyperspectral measurement and user input.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including Instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A system for evaluating a vehicle, comprising:
a plurality of hyperspectral sensors located in the vehicle;
a system for fusing hyperspectral sensor data with user data into a feature vector;
a support vector machine having a set of models, wherein the support vector machine implements a selected model based on the feature vector and outputs an evaluation based on data in the feature vector and the selected model, the evaluation includes a prescriptive plan pertaining to a pre-breakdown vehicle problem and a set of system actions, and the vehicle performs the set of system actions in response to the evaluation; and
a system for training the set of models.

2. The system of claim 1, wherein the user data is obtained from an operator of the vehicle, and wherein the user data includes at least one of: user feedback, a user preference, and a user driving style.

3. The system of claim 1, wherein the system for fusing hyperspectral sensor data with user data into a feature vector also fuses ecosystem data into the feature vector.

4. The system of claim 3, wherein the ecosystem data includes one of weather conditions and smog levels.

5. The system of claim 1, wherein the support vector machine projects the feature vector into a state space using a kernel function, and wherein the kernel function determines the selected model based on data in the feature vector.

6. The system of claim 1, wherein the system for training the set of models includes both online training and offline training.

7. The system of claim 1, wherein the prescriptive plan includes one of proposed maintenance, a suggested driving technique, and an operator test.

8. A program product stored on a non-transitory computer readable storage medium for evaluating a vehicle, comprising:
- program code for obtaining hyperspectral sensor data from hyperspectral sensors located in the vehicle;
- program code for fusing the hyperspectral sensor data with user data into a feature vector;
- program code for implementing a support vector machine having a set of models, wherein the support vector machine implements a selected model based on the feature vector and outputs an evaluation based on data in the feature vector and the selected model, the evaluation includes a prescriptive plan pertaining to a pre-breakdown vehicle problem and a set of system actions, and the vehicle performs the set of system actions in response to the evaluation; and
- program code for training the set of models.

9. The program product of claim 8, wherein the user data is obtained from an operator of the vehicle, and wherein the user data includes at least one of: user feedback, a user preference, and a user driving style.

10. The program product of claim 8, wherein the program code for fusing hyperspectral sensor data with user data into the feature vector also fuses ecosystem data into the feature vector.

11. The system of claim 10, wherein the ecosystem data includes one of weather conditions and smog levels.

12. The program product of claim 8, wherein the support vector machine projects the feature vector into a state space using a kernel function, and wherein the kernel function determines the selected model based on data in the feature vector.

13. The program product of claim 8, wherein the program code for training the set of models includes both online training and offline training.

14. The program product of claim 8, wherein the prescriptive plan includes one of proposed maintenance, a suggested driving technique, and an operator test.

15. A method of evaluating a vehicle, comprising:
- obtaining hyperspectral sensor data from hyperspectral sensors located in the vehicle;
- fusing the hyperspectral sensor data with user data into a feature vector; and
- providing a support vector machine having a set of models, wherein the support vector machine implements a selected model based on the feature vector and outputs an evaluation based on data in the feature vector and the selected model, the evaluation includes a prescriptive plan pertaining to a pre-breakdown vehicle problem and a set of system actions, and the vehicle performs the set of system actions in response to the evaluation.

16. The method of claim 15, further comprising training the set of models.

17. The method of claim 15, wherein the user data is obtained from an operator of the vehicle, and wherein the user data includes at least one of: user feedback, a user preference, and a user driving style.

18. The method of claim 15, wherein the fusing of hyperspectral sensor data with user data into the feature vector also fuses ecosystem data into the feature vector.

19. The system of claim 18, wherein the ecosystem data includes one of weather conditions and smog levels.

20. The method of claim 15, wherein the prescriptive plan includes one of proposed maintenance, a suggested driving technique, and an operator test.

* * * * *